United States Patent [19]
Mackenzie

[11] Patent Number: 6,156,742
[45] Date of Patent: *Dec. 5, 2000

[54] EMERGENCY CONTRACEPTIVE KIT

[75] Inventor: Roderick L. Mackenzie, Bonita Springs, Fla.

[73] Assignee: Gynetics Inc., Somerville, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/905,055

[22] Filed: Aug. 1, 1997

Related U.S. Application Data

[63] Continuation of application No. 08/648,874, May 16, 1996, abandoned.

[51] Int. Cl.[7] .................................................. A61K 31/56
[52] U.S. Cl. ............................ 514/170; 514/171; 514/843
[58] Field of Search ..................................... 514/170, 171, 514/843

[56] References Cited

U.S. PATENT DOCUMENTS

| | | |
|---|---|---|
| 3,595,620 | 7/1971 | Gordon et al. . |
| 3,678,117 | 7/1972 | Middleton . |
| 3,845,214 | 10/1974 | Gallo et al. . |
| 3,864,365 | 2/1975 | Grosse et al. . |
| 4,256,629 | 3/1981 | Bahl . |
| 4,313,871 | 2/1982 | Bahl . |
| 4,390,633 | 6/1983 | Merilan et al. . |
| 4,508,829 | 4/1985 | Sulitzeanu . |
| 4,578,385 | 3/1986 | Cormier . |
| 4,665,096 | 5/1987 | Oraa et al. . |
| 4,670,426 | 6/1987 | Zor et al. . |
| 4,965,191 | 10/1990 | Warren, III et al. . |
| 5,096,265 | 3/1992 | Portman et al. . |
| 5,145,789 | 9/1992 | Corti et al. . |
| 5,185,128 | 2/1993 | McClune et al. . |

OTHER PUBLICATIONS

Medline Abstract, AN 85075349 (1984), Yuzpe, A. A.
The Merck Index, Budavari et al., Merck & Co., Inc., Rahway, N.J. (1989) p. 1060.
Physicians Desk Reference (PDR Electronic Library), Entry for Preven. Emergency Contraceptive Kit (Gynetics), pp. 1–18, Jun. 1999.
*Emergency Contraception*—(1995) Family Planning Association of London.
"Emergency Hormonal Contraception," Manual of Medical Standards amd Guidelines, Section III–D–1, Planned Parenthood Federation of America, Inc. Feb. 1995, 1–5.

*Primary Examiner*—Minna Moezie
*Assistant Examiner*—S. Wang
*Attorney, Agent, or Firm*—Lerner, David, Littenberg, Krumholz, & Mentlik, LLP

[57] ABSTRACT

A kit which is adapted and designed to provide both data on the current reproductive status of a patient, and contraception for those who are not pregnant, but recently engaged in unprotected sex.

7 Claims, No Drawings

યુ.એસ. 6,156,742

EMERGENCY CONTRACEPTIVE KIT

This is a continuation of application Ser. No. 08/648,874, filed May 16, 1996, now abandoned.

FIELD OF THE INVENTION

The present invention relates to the fields of medicine, pharmacology and contraception and specifically provides kits which allow women to evaluate their current reproductive status prior to, and as a prelude to, taking certain contraceptive steps following unprotected sex.

BACKGROUND OF THE INVENTION

Unintentional pregnancies occur for any number of reasons. Certainly, they can occur following sexual intercourse when neither party uses a contraceptive device or drug. However, this is by no means, the only reason for unintended pregnancies. Condoms are known to break; diaphragms to slip; and traditional contraceptive pills are, by their own admission, not 100 percent effective, even when taken properly. Moreover, when pills are missed, particularly with the newer, low-dose products, the risk of pregnancy increases substantially. In fact, each year in the U.S. alone, approximately 750,000 pregnancies occur to women using traditional oral contraceptive regimens. Of course, some of these pregnancies occur because the patient has failed to completely and dogmatically follow the prescribed pharmaceutical regimen.

In some countries, particularly Europe, emergency contraceptive ("EC") pills are an available treatment for women who are concerned they may have become pregnant by their most recent unprotected sexual encounter. These pills are intended for administration within days, and preferably within hours after unprotected sex and often contain relatively high doses of for example, a progestin and/or an estrogen. Reports in the scientific literature describe other drugs which may be effective for emergency contraception as well. Dosages and protocols will vary with the drug(s) used. However, in each case, the "pills" help to prevent pregnancy, i.e. either preventing a fertilized ovum from implanting in the lining of the uterus and/or depending on the timing of intercourse, preventing the sperm from fertilizing an egg.

Doctors in countries that allow the use of the EC pill will often ask patients when their last period occurred during an office visit. Unfortunately, there are at least two significant drawbacks to this approach. First, a woman may or may not have an accurate recollection of when her last menstrual period occurred. Furthermore, a woman can have a period and still be pregnant. Second, EC pills are not always dispensed by doctors for immediate use. To increase compliance and to provide a higher rate of efficacy, doctors may provide EC pills to their patients well in advance of a sexual encounter. As a result, these pills may sit in a purse or medicine cabinet for weeks or even months before use. In the United States, there is currently no FDA approved version of EC pills. However, gynecologists, obstetricians and other licensed family planning professionals may create their equivalents out of multiple doses from a package of 21 traditional birth control pills, verbally instructing their patients to take a certain number of pills, in the future, if necessary, following unprotected sex. In either instance, this allows the patient to receive treatment even when a doctor is unavailable. Of course, this also removes all possible safeguards which should be employed before any type of medical treatment is undertaken.

Another common problem associated with EC pills is the incidence of nausea which occurs in a significant percentage of patients. Some patients experience vomiting after taking the EC pill. This is not only uncomfortable, but may also compromise the efficacy of the contraceptive. Unless steps are taken to prevent the loss of bioavailable drug from the digestive tract and/or proper medical instruction is given as to how to react in such cases, there is a greater chance of pregnancy. Certainly, a woman who has taken an EC pill and has had an adverse effect, is less likely to take the steps to assure efficacy, including taking more EC pills.

In addition to the problems previously discussed, other problems with the use of EC pills include the possibility that a woman is indeed already pregnant when she takes an EC pill. Oral contraceptive formulations, such as one made from combinations of estrogen and progestin, used postcoitally, will not cause an abortion of that pregnancy, i.e., will not terminate pregnancy if the fertilized ovum has already implanted within the lining of the uterus. A woman in such a position, however, after taking an EC pill, may believe that she has successfully avoided pregnancy and delay seeking immediate and proper medical attention for her condition. The same woman may then commence activities, or return to her normal routine of taking daily contraceptive pills, as well as other prescribed and over-the-counter medicines, or may consume alcohol, commence recreational drug use or undertake other activities which might be detrimental to her pregnancy, without first seeking the appropriate medical care. Many of these activities may cause problems to the pregnancy, and may affect the health or well-being of any child born from that pregnancy. It is always essential that a woman receive appropriate medical care and counseling once a pregnancy is discovered and before continuing with various medications and activities.

Therefore, there remains a need for an easy and convenient way to insure that the taking of an EC pill will be effective in preventing a pregnancy. There is also a great need for an easy, convenient, cost-effective and efficacious way to advise women to seek medical care prior to taking an EC pill, continuing on their normal contraceptive regimen, taking any other medication, or engaging in activity which should be discussed with a medical professional, when indeed she is pregnant.

SUMMARY OF THE INVENTION

The present invention provides a safe, convenient, effective and cost-effective way to assist women in determining whether or not to use an EC pill, or its functional equivalent. The present invention will advise a woman of whether or not an EC pill will be efficacious in preventing pregnancy. The present invention also provides a safe, convenient, easy-to-use and cost-effective way to advise women to seek medical help prior to taking any further actions following unprotected sex. The present invention also anticipates the effects that EC pills might have on a patient and provides both the necessary medication, and the necessary information, to assure that a woman can continue with an efficacious course of treatment.

Specifically, the present invention provides a contraception kit adapted for use after unprotected sexual intercourse. The kit includes at least one pregnancy detection device designed to detect pregnancy at a particular stage and a contraceptive designed to prevent pregnancy. In a particularly preferred embodiment, the contraceptive kit includes a pregnancy detection device designed to detect pregnancy as soon as possible after the implanting of a fertilized egg in the wall of the uterus of the patient. The contraceptive is designed to prevent pregnancy, (i.e. the implantation of a fertilized egg), and must be used before the implanting of the fertilized egg in the lining of the uterus.

Most preferably, the contraceptive is an orally administerable pharmaceutical and the contraceptive kit includes a pregnancy detection device designed to detect pregnancy by detecting the presence of human chorionic gonadotropin ("hCG") which is produced in a woman's body following the implanting of a fertilized egg in the lining of the uterus. Of course, hCG production may start at fertilization and increase in concentration daily. However, the preferred test only detects hCG at levels which would result upon implantation of a fertilized egg in the lining of the uterus.

In a further embodiment, the present invention also provides a means for retarding the involuntary expulsion of the contraceptive drug from the digestive tract. This means can include the inclusion of an appropriate amount of an anti-emetic or anti-nausea drug. The anti-emetic can be taken with the contraceptive as a prophylactic measure, or may be administered with subsequent or repeat dosages of contraceptive in women who do experience nausea or "throw-up".

Other means for retarding the involuntary expulsion of the contraceptive drug include the use of buffering and/or enteric coatings. The kit in accordance with the present invention provides a perfectly matched set of pregnancy detection devices, contraceptives, and optionally, an anti-emetic. For example, a particularly preferred embodiment of the present invention provides a pregnancy detection device which is designed to detect the presence of hCG in a woman's urine. This test can be conveniently used by a woman in the privacy of her own home, which aids in compliance. Devices which detect hCG are valuable tools because hCG is produced once pregnancy has started, by the growing placenta immediately following the embedding of a fertilized egg in the wall of the uterus. HCG is produced very quickly after pregnancy begins. Therefore, pregnancy can be determined early, before a menstrual period is missed. More importantly in the context of the present invention, such a pregnancy detection device can be coupled with a specific type of contraceptive formulation which is only contraceptively effective prior to pregnancy.

It is critical that both the contraceptive formulation and the pregnancy detection device be selected to work in this coordinated fashion. If, for example, a different form of pregnancy detector was used, it is more likely that a woman using a kit will receive an indication that she is not pregnant shortly after unprotected sex, when indeed she is in the earliest phase of pregnancy. Therefore, she will take the EC pill provided with the kit thinking that she is not yet pregnant. Unfortunately, this will not have the intended effect and, believing she is not pregnant, the patient may delay seeking appropriate medical supervision.

DETAILED DESCRIPTION OF THE PREFERRED EMBODIMENTS

Pregnancy in accordance with the present invention is defined as the condition of a woman after a fertilized ovum or egg has successfully implanted itself in the lining of the uterus. It is not unusual for an egg to be fertilized following unprotected sex, and yet never become embedded. In that case, the fertilized egg is then harmlessly excreted. The egg may also embed too late in a woman's cycle and may be shed along with the uterine lining each month. While in each instance a fertilized egg was present, neither of these natural and frequent conditions constitute "pregnancy" as defined herein.

The contraceptive used in accordance with the present invention may prevent a fertilized ovum from embedding in the lining of the uterus. The contraceptive used could also act to prevent the ovum from being fertilized or inhibit sperm's ability to fertilize an ovum.

"Unprotected sex" or "unprotected sexual intercourse" refers to sexual intercourse which results in a man's sperm being allowed to continue through a woman's reproductive tract such that it can fertilize an ovum. Unprotected sexual intercourse may occur by consenting adults deciding not to use any form of birth control. Unprotected sex may also result, in accordance with the present invention, from the improper use of a condom, diaphragm, or other mechanical device, drugs or chemicals, or their failure during intercourse. Unprotected sexual intercourse also results from the failure of contraceptive drugs or their incorrect use. Unfortunately, unprotected sex may also occur in cases of rape and incest.

The phrase "detecting pregnancy at a particular stage" refers to, amongst other things, detecting pregnancy at a point before, or as near as possible after the embedding of a fertilized egg in the wall of the uterus. Preferably, the "particular stage" in question is defined in terms of the concentration of hCG in the blood. For example, in one embodiment, the "particular stage" is the point at which about 20 to about 50 milliInternational Units/ml ("mIU/ml") of hCG are detectable.

The contraceptive kit of the present invention includes at least one pregnancy detection device designed to detect pregnancy at a particular stage which is as close, prior to, or just after, the time of implantation of the fertilized egg. Preferably, the pregnancy detection device is designed to detect the presence of hCG, and, even more preferably, hCG in amounts of less than about 50 mIU/ml. A particularly preferred pregnancy detection device is one which is designed to detect the presence of hCG in a concentration of as low as about 20 to about 25 mIU/ml or even less. Tests for hCG include those set forth in U.S. Pat. No. 4,508,829 issued to Sulitzeanu; U.S. Pat. No. 4,313,871 issued to Bahl; U.S. Pat. No. 5,145,789 issued to Corti et al.; U.S. Pat. No. 5,185,128 issued to McClune et al.; U.S. Pat. No. 4,256,629 issued to Bahl; and U.S. Pat. No. 4,965,191 issued to Warren, III et al.; all of which are hereby incorporated by reference. Devices which are useful in accordance with the present invention are commercially available.

Preferably, the pregnancy detection device in accordance with the present invention is useful in determining the presence of some physiological agent indicative of pregnancy, such as hCG, which is found in a woman's urine. However, it is possible to test for agents found in the blood, saliva, tears and the like. The pregnancy detection device in accordance with the present invention also preferably has at least a positive and/or a negative control so that a woman can determine whether or not the test is performing properly. Two or more such testing devices, each including both positive and negative controls, could be provided as the chance of both being inoperable, and therefore, the chances of false readings, are greatly reduced.

The contraceptive included within the kit of the present invention will depend largely upon the type of pregnancy detection device used. Preferably, in accordance with the present invention, the contraceptive should be selected such that it will interfere with the fertilization of an egg, inhibit sperm or prevent the embedding of an ovum in the wall of the uterus. Most preferably, the contraceptive used will not be such as to cause an abortion after pregnancy has been achieved. Postcoital contraceptive pharmaceutical compositions of this type include those disclosed in U.S. Pat. No. 4,670,426 to Zor et al.; U.S. Pat. No. 4,578,385 to Cormier; U.S. Pat. No. 3,864,365 to Grosse et al.; U.S. Pat. No. 3,845,214 to Gallo et al.; and U.S. Pat. No. 3,678,117 to Middleton, all of which are hereby incorporated by reference. EC pill formulations which are commercially available include TETRAGYNON, sold in Germany and manufactured by Schering AG, and PC4 sold in the United Kingdom by Schering Health Care Limited, Burgess Hill, West Sussex. PC4 and TETRAGYNON include four tablets, each containing Levonorgestrel (0.25 mg) in 0.5 mg, Norgestrel and Ethinyloestradiol (0.05 mg.) Such contraceptives are orally administerable pharmaceutical dosage forms which are administered over a limited period of time immediately following unprotected sex. Usually this time period is less than five days. Most preferably, administration of such pharmaceutical dosage forms begins within 24 hours of unprotected sex and after a woman has determined that she is not pregnant by using the included pregnancy detection device. Depending upon the pharmaceutical used, a single or multiple dose may be necessary following unprotected sex. For example, in accordance with the present invention, the kit may include 4 to 6 contraceptive pills, each of which contains, for example, 0.25 mg of Levonorgestrel and 0.05 mg of Ethinyloestradiol. White solid dosage forms such as pills, capsules, or gel caps are preferred, the contraceptive of the present invention can be provided in any convenient form. For example, the contraceptive could be provided as a powder, a liquid, or a liquid slurry of micro-encapsulated active.

Two pills should be taken immediately after determining that the patient is not pregnant and as soon as possible after unprotected sex. Two further doses should be taken twelve hours later. In general, the tablets should be provided over a period of between about 24 and about 120 hours. The amounts and the rate of administration will depend in large part on the specific contraceptive drugs used.

Contraceptively equivalent amounts of other progestins and estrogens may be used. Progestins such as norethindrone, norgestimate, desogistrel, gestrodene, medroxyprogesterone acetate and progesterone, for example, may be used in well known ratios to levonogestrel. For example, pills containing 0.50 mg of norgestimate and 0.05 mg of ethinylestradiol would be contraceptively equivalent to the preferred. Similarly 0.05 mg of ethinylestradiol may be replaced by 0.08 mg of mestranol. Higher doses of progestin, e.g., 0.75 mg of levongestrel will/may not require an estrogen to be effective.

Of course, it is also possible to use other contraceptives such as those which may be applied intravaginally immediately after coitus. See Oráa, deceased et al., U.S. Pat. No. 4,665,096, the text of which is hereby incorporated by reference.

The kit of this invention should also include simple, clear and explicit directions explaining to a patient how to use the pregnancy detection device, how to insure that it is working accurately, and a warning not to take any medication, including the contraceptive included with the kit, if there is any question as to the accuracy of the pregnancy detection device. In the event of such problems, or in the event that pregnancy is indicated by properly functioning devices, the patient should be instructed not to take the included contraceptive, not to continue with her normal contraceptive regimen, or indeed engage in a host of activities, until after having first consulted a physician. If the properly functioning devices indicate that a woman is not pregnant, clear directions are then provided for the proper administration of the contraceptive included in the kit.

Of course, the use of this pregnancy detection device will have benefits in terms of both detecting pregnancy and determining whether or not the contraceptive supplied with the kit will be effective. Additionally, a positive reading of an hCG based test may also indicate the presence of an ectopic pregnancy or a malignancy, both very dangerous medical conditions. The possibility of either of these conditions further underscores the need for the present invention.

The kits in accordance with the present invention may be supplied to doctors' offices, pharmacies, or for home use. They may include in addition to instructions: pregnancy detection devices; contraceptives; and any other component which may be useful, such as, for example: applicators, cups, test papers, timers, absorbent pads, bottles, jars and the like. Also, preferably, the kit will include a toll free number which will place a patient who has questions regarding the kit, its operation, or the results obtained, in immediate contact with a trained medical professional such as a registered nurse or a doctor.

As previously discussed, in some percentage of women who take EC formulations, vomiting may occur within two hours after swallowing either the first or the second dose. If the patient does experience vomiting, an additional dose should be taken at once. For that very reason, it may be advantageous to provide six tablets while only four are absolutely necessary for efficacy. However, it is difficult to convince a woman who has just vomited to take additional medication when it is that very medication that has caused her discomfort. To remedy this situation, a means for retarding the unintended or involuntary expulsion of the administered contraceptive may be provided as part of the kit. This means can take a number of forms. First, an anti-nausea formulation or anti-emetic can be provided along with the contraceptive and the pregnancy detection device within the kit. Several anti-nausea or anti-emetic formulations are possible such as, over-the-counter or prescription strength scopolamine, cyclizine, dimenhydrinate, and the like. These drugs are administered in the amounts normally prescribed for nausea.

There are two possible ways to administer anti-emetics in combination with the contraceptives in accordance with the present invention. Either the anti-emetic can be administered prophylactically with each dose of the contraceptive to attempt to minimize discomfort at the very start. The downside of this protocol is the necessity in providing anti-emetics which may not be necessary, increasing the size and cost of the kit. In addition, it is always desirable to administer as little medication as medically necessary at any given time. Since the majority of woman do not experience sufficient nausea that causes vomiting, most women would be subjected to an unnecessary, if harmless, dose of an anti-emetic.

Alternatively, anti-emetics could be provided with instructions to take the anti-emetics with subsequent doses of contraceptives, only after vomiting has been induced. The provision of the anti-emetic in accordance with the present invention is extremely important as is the selection of an appropriate medication. It is critical that a woman be confident enough in the efficacy of the formulations to encourage her to actually continue with the prescribed contraceptive protocol, even after vomiting. For that reason, care should be taken in selecting the specific type of anti-emetics to be administered.

Other means for retarding the unwanted expulsion of the contraceptive include, for example, providing a buffering agent as part of the formulation. Alternatively, one could coat either the solid dosage form or the active drug with, for example an enteric coating. In the latter case, because drug release will be avoided until dissolution in the intestines, even if a woman should vomit, she will not expel the drug.

We claim:

1. A contraceptive kit for use by a woman after unprotected sexual intercourse, comprising:

one pregnancy detection device that detects hCG in urine in an amount between about 20 and about 25 mIU/ml;

an emergency contraceptive in an amount that prevents a single pregnancy only, wherein said contraceptive comprises four pills, each of which contains 0.25 mg levonorgestrel and 0.05 mg ethinyl estradiol; and directions explaining to the woman how to use the pregnancy detection device and warning the woman not to take the emergency contraceptive if pregnancy is indicated by the pregnancy detection device.

2. The contraceptive kit of claim 1 wherein said pregnancy detection device includes at least one control.

3. The contraceptive kit of claim 2 wherein said control includes at least one positive control.

4. The contraceptive kit of claim 2 wherein said control includes at least one negative control.

5. The contraceptive kit of claim 1 further comprising at least one means for retarding the unwanted expulsion of the emergency contraceptive.

6. The contraceptive kit of claim 5 wherein said means for retarding the unwanted expulsion of the contraceptive is an anti-emetic.

7. The contraceptive kit of claim 5 wherein said means for retarding the unwanted expulsion of the contraceptive is an enteric coating.

* * * * *